United States Patent [19]

Martin et al.

[11] 4,384,043

[45] May 17, 1983

[54] PROCESS FOR PRODUCING THE ANTIBIOTIC NOSIHEPTIDE

[75] Inventors: John H. E. J. Martin, New City, N.Y.; David P. Labeda, Monsey; Joseph D. Korshalla, Pearl River; Donald B. Borders, Suffern, all of N.Y.; Raymond T. Testa, Cedar Grove, N.J.

[73] Assignee: American Cyanamid Company, Stamford, Conn.

[21] Appl. No.: 298,674

[22] Filed: Sep. 2, 1981

[51] Int. Cl.$^3$ .................... C12P 21/04; C12P 17/18; C12N 1/20; C12R 1/465

[52] U.S. Cl. .................... 435/71; 435/119; 435/253; 435/886

[58] Field of Search ............ 435/886, 71, 119, 253

[56] References Cited

U.S. PATENT DOCUMENTS

| | | | |
|---|---|---|---|
| 3,155,581 | 11/1964 | Pinnert et al. | 435/886 |
| 3,155,583 | 11/1964 | Rao et al. | 435/886 |
| 3,190,801 | 6/1965 | Arcamone et al. | 435/886 |
| 3,264,185 | 8/1966 | Marsh et al. | 435/886 |
| 3,317,400 | 5/1967 | Reusser et al. | 435/886 |
| 3,880,827 | 4/1975 | Eble et al. | 435/886 |

FOREIGN PATENT DOCUMENTS 768971  2/1957  United Kingdom ............... 435/886

OTHER PUBLICATIONS

Buchanan et al. (ed): *Bergey's Manual of Determinative Bacteriology*, 8th ed., Waverly Press, Inc., Baltimore, 1974, pp. 820–827.

*Primary Examiner*—Alvin E. Tanenholtz
*Assistant Examiner*—James Martinell
*Attorney, Agent, or Firm*—Anne M. Rosenblum

[57] ABSTRACT

This disclosure describes a novel process for the production of the known antibiotic nosiheptide using a new strain of *Streptomyces glaucogriseus* and mutants thereof.

7 Claims, No Drawings

PROCESS FOR PRODUCING THE ANTIBIOTIC NOSIHEPTIDE

BACKGROUND OF THE INVENTION

1. Field of Invention

The present invention relates to a novel process for the production of the known antibiotic nosiheptide using a new strain of Streptomyces glaucogriseus and mutants thereof.

2. Description of the Prior Art

The applicants are not aware of any prior art patents or publications which, in their respective judgment, should be deemed to anticipate or render obvious the process or the microorganism described and claimed herein. By way of background, U.S. Pat. No. 3,155,581 to Rhone-Poulenc S. A. is cited, wherein the product nosiheptide (designated therein as antibiotic 9671-RP) and a method for its manufacture by the aerobic cultivation of the microorganism Streptomyces actuosus NRRL 2954 are claimed. The utility of nosiheptide as an antibacterial agent is disclosed in that patent. Also, Pascard, C., et al., J. A. C. S. 99:19 (Sept. 14, 1977) discloses the structure of nosiheptide.

BRIEF SUMMARY OF THE INVENTION

The instant invention relates to a new strain of Streptomyces glaucogriseus, sp. nov., and mutants thereof derived spontaneously or by conventional mutagenic or recombinant techniques. This invention further concerns a new process for the production of the antibiotic nosiheptide by fermentation, under controlled conditions, as well as the methods for recovery and concentration thereof from crude solutions.

DETAILED DESCRIPTION OF THE INVENTION

In accordance with the present invention, there is provided a new process for the production of the known antibiotic nosiheptide by the cultivation, under controlled conditions, of a new strain of Streptomyces glaucogriseus, sp. nov.

This new antibiotic-producing strain was isolated from a soil sample collected in Bernalillo County, N. Mex. and is maintained in the culture collection of the Lederle Laboratories Medical Research Division, American Cyanamid Company, Pearl River, N.Y. 10965, as culture number BP-189. A viable culture of this new microorganism has been deposited with the Culture Collection Laboratory, Northern Utilization Research and Development Division, U.S. Department of Agriculture, Peoria, Ill. 61604, and has been added to its permanent collection. It is freely available to the public from this depository under its accession number NRRL 12514.

The following is a general description of the microorganism Streptomyces glaucogriseus NRRL 12514, based on diagnostic characteristics observed. Observations were made of the cultural, physiological and morphological features of the organism in accordance with the methods detailed by E. B. Shirling and D. Gottlieb, Methods for the Characterization of Streptomyces species, Internat. J. Syst. Bacteriol. 16:313-340 (1966). Media used in the study were selected from those recommended for the taxonomic study of actinomycetes and soil bacteria by T. G. Pridham, et al., A Selection of Media for Maintenance and Taxonomic Study of Streptomycetes, Antibiotics Ann. 947-953 (1956-1957) and R. E. Gordon, The Taxonomy of Soil Bacteria, THE ECOLOGY OF SOIL BACTERIA, pp. 293-321 (T. G. R. Gray and D. Parkinson eds.), Liverpool University Press, Liverpool, England (1967), respectively, Chemical composition of the cell walls of the culture was determined using the method of H. A. Lechevalier, et al., Chemical Composition as a Criterion in the Classification of Actinomycetes, Adv. Appl. Microbiol. 14:47-72 (1971), as modified by J. L. Staneck and G. D. Roberts, Simplified Approach to Identification of Aerobic Actinomycetes by Thin-layer Chromatography, Appl. Microbiol. 28:226-234 (1974). Underscored descriptive colors are taken from K. L. Kelly and D. B. Judd, Color, Universal Language and Dictionary of Names, Nat. Bur. Stand. (U.S.) Spec. Publ. 440, Washington, D.C. (1976) and the accompanying Inter-Society Color Council, National Bureau of Standards Centroid Color Charts. Details on the following general description of the culture are recorded in Tables I-V below.

MICROMORPHOLOGY

Spores are formed in long spiral chains (Spira) on aerial sporophores. The spores are ovoid (0.6-0.8 micro$\times$1.0-1.2 micron) and the surface of the mature spores is ornamented with spines approximately 200 nanometers in length.

CELL WALL COMPOSITION

Whole cell hydrolysates of this culture contain the L,L-isomer of diaminopimelic acid, placing it in the Type I cell wall group of Lechevalier, et al. (1971). This is typical of all Streptomyces species.

AMOUNT OF GROWTH

Good growth is observed on most media; moderate growth is observed on asparagine-dextrose agar, Benedict's agar, Czapek's-casamino acid agar, Emerson agar and glycerol-casein agar; poor growth is observed on nutrient agar.

AERIAL MYCELIUM AND/OR EN MASSE SPORE COLOR

Aerial mycelium is white; spore masses are blue shades ranging from 189. bluish white to 190. light bluish gray on most media but are green shades ranging from 153. greenish white to 154. light greenish gray on several other media. Sporulation is absent on Benedict's and Emerson agar, but ranges from sparse to heavy on other media.

SOLUBLE PIGMENTS

Produced on all media evaluated except nutrient agar; colors range from yellow through orange and red to brown, depending upon the medium. Dark wine-red soluble pigments are produced on oatmeal and malt extract media.

REVERSE COLOR

In brown shades, ranging from grayish brown to dark reddish-brown.

PHYSIOLOGICAL REACTIONS

Nitrates not reduced to nitrites; moderate liquefaction of gelatin in 14 days; litmus milk weakly peptonized in 14 days; melanoid pigments produced on both peptone-yeast extract-iron agar and tyrosine medium. Hydrolysis of adenine, hypoxanthine, and tyrosine, but not guanine or xanthine in 7 days. Carbohydrate utilization as per the method of T. G. Pridham and D. Gottlieb, The Utilization of Carbon Compounds by Some Actinomycetales as an Aid for Species Determination, J. Bacteriol., 56:107–114 (1948): good utilization of adonitol, galactose, glucose, inositol, maltose, melibiose, rhamnose and salicin; moderate utilization of arabinose, fructose, lactose, mannitol, mannose, raffinose, ribose, sucrose, trehalose, and xylose; poor utilization of dulcitol; no utilization of glycerol or melezitose. Growth observed at 10% but not 13% NaCl.

Streptomyces glaucogriseus BP-189 was compared with Streptomyces reference cultures from the Lederle Culture Collection which have similar characteristics, i.e., blue spores (B), chromogenic (C+), and having spiral spore chains (S) with spiny spores (SPY). The Rhone-Poulenc culture Streptomyces actuosus, a gray, smooth-spored (GY; SM) strain which produces nosiheptide, was also examined.

Isolate BP189, which is a blue-series streptomycete, bears no resemblance to Streptomyces actuosus NRRL 2757, a gray-series streptomycete, other than in the production of the antibiotic nosiheptide. Moreover, this isolate does not closely resemble any of the described spiny, blue-spored Streptomyces species whose spores are borne in spiral chains, including Streptomyces afghaniensis ATCC 23871, the taitomycin producer. Thus it was designated as a new species of the blue-series Streptomyces to be named Streptomyces glaucogriseus, sp. nov., because of the blue-gray to green-gray color of the spore masses on many media.

The observations of these cultures, made after 14 days of growth on yeast-extract-malt-extract agar, are recorded in Table I.

TABLE 1

Morphological Comparisons of Streptomyces glaucogriseus NRRL 12514 with Other Reference Cultures

| Culture | Spore Color | Soluble Pigment | Reverse Color | Growth |
|---|---|---|---|---|
| GY;S;C+;SM | | | | |
| RC50 S. actuosus NRRL 2757 | Medium gray | Orange-brown | Grayish brown | Good |
| B;S;C+;SPY | | | | |
| RC51 S. afghaniensis ATCC 23871 | Bluish white | Orange-red | Dark reddish-brown | Good |
| BB643 S. azureus ATCC 14921 | Light bluish-gray | None | Light yellowish-brown | Good |
| AE4 S. chartreusis ATCC 14922 | Pale blue | Yellow | Brownish-orange | Good |
| BE821 S. chartreusis NRRL B-2199 | Grayish-green | Orange-yellow | Moderate brown | Good |
| BB102 S. coeruleofuscus PSA 187 | Light bluish-gray | Reddish-brown | Brownish-orange | Good |
| BB103 S. coeruleorubidus ATCC 13740 | Very pale blue | Orange | Light brown | Good |
| BB104 S. coerulescens PSA 168 | Pale blue | Yellow | Light yellowish-brown | Good |
| BP189 S. glaucogriseus | Light bluish-gray to light greenish-gray | Dark red | Moderate reddish-brown | Good |

TABLE II

CULTURAL CHARACTERISTICS OF Streptomyces glaucogriseus NRRL 12514

INOCULATION — INCUBATION 14 days — TEMPERATURE 28° C.

| MEDIUM | AMOUNT OF GROWTH | AERIAL MYCELIUM AND/OR SPORES | SOLUBLE PIGMENT | REVERSE COLOR | REMARKS |
|---|---|---|---|---|---|
| Asparagine Dextrose Agar | Moderate | White aerial mycelia becoming 153. greenish-white. Sporulation light. | Orange-yellow | 53. moderate orange | |
| Bennett's Agar | Good | White aerial mycelia becoming 190. light bluish gray. Sporulation heavy | Red-brown | 47. dark grayish reddish brown | |
| Benedict's Agar | Moderate | Sparse white aerial mycelia. No sporulation. | Yellow | 89. pale yellow | |
| Czapek's Solution Agar | Good | White to 92. yellowish white aerial mycelia becoming 189. bluish white. Moderate sporulation. | Red-brown | 39. grayish reddish orange | |
| Czapek's-Casamino Acid Agar | Moderate | White aerial mycelia becoming 190. light bluish gray. Moderate sporulation. | Red-brown | 39. grayish reddish orange | |
| Emerson's Agar | Poor to moderate | No aerial mycelia; substrate mycelia 92. yellowish white | Brown | 56. deep brown | |
| Glycerol-Casein Agar | Moderate | White aerial mycelia becoming 153. greenish white to 189. bluish white. Moderate sporulation. | Brownish | 76. light yellowish brown | |
| Hickey-Tresner Agar | Good | White aerial mycelia becoming 153. greenish white to 154. light grayish green. Sporulation heavy. | Reddish-brown | 47. dark grayish reddish brown | |

TABLE II-continued

CULTURAL CHARACTERISTICS OF Streptomyces glaucogriseus NRRL 12514

| | INOCULATION | INCUBATION 14 days | | TEMPERATURE 28° C. | |
|---|---|---|---|---|---|
| MEDIUM | AMOUNT OF GROWTH | AERIAL MYCELIUM AND/OR SPORES | SOLUBLE PIGMENT | REVERSE COLOR | REMARKS |
| Inorganic-Salts Starch Agar | Good | White aerial mycelia becoming 153. greenish white to 154. light greenish gray. Moderate sporulation. | Red | 40. strong reddish brown | |
| Nutrient Agar | Poor | Sparse white aerial mycelia with scattered patches of 184. very pale blue sporulation. | None | Colorless | |
| Oatmeal Agar | Good | White aerial mycelia becoming 153. greenish white to 154. light greenish gray. Sporulation heavy. | Dark red | 47. dark grayish reddish brown | |
| Tomato Paste-Oatmeal Agar | Good | White aerial mycelia becoming 154. light greenish gray to 190. light bluish gray. Heavy sporulation. | Dark red | 47. dark grayish reddish brown | |
| Yeast Extract-Malt Extract Agar | Good | White aerial mycelia becoming 190. light bluish gray to 154. light greenish gray. Sporulation heavy. | Dark red | 43. moderate reddish brown | |

TABLE III

MICROMORPHOLOGY OF Streptomyces glaucogriseus NRRL 12514

| MEDIUM | AERIAL MYCELIUM AND/OR SPORIFEROUS STRUCTURES | SPORE SHAPE | SPORE SIZE | SPORE SURFACE |
|---|---|---|---|---|
| Yeast Extract | Spore chains arise as spiral chains from aerial sporophores (Spira) | Ovoid to spherical | 0.6–0.8 μm × 1.0–1.2 μm | Spiny |

TABLE IV

MISCELLANEOUS PHYSIOLOGICAL REACTION OF Streptomyces glaucogriseus NRRL 12514

| | INOCULATION | | TEMPERATURE 28° C. | |
|---|---|---|---|---|
| MEDIUM | INCUBATION PERIOD | AMOUNT OF GROWTH | PHYSIOLOGICAL REACTION | REMARKS |
| Peptone-Yeast Extract-Iron Agar (ISP-6) | 48 hours | Good | Strong production of melanoid pigments | |
| Tyrosine Medium (ISP-7) | 48 hours | Good | Moderate production of melanoid pigments | |
| Litmus Milk | 7 days | Good | Slight peptonization | |
| | 14 days | Good | Slight peptonization | |
| Nutrient Gelatin | 7 days | Good | Slight hydrolysis | |
| | 14 days | Good | Moderate hydrolysis | |
| Organic Nitrate Broth | 7 days | Good | Negative | |
| | 14 days | Good | Negative | |
| NaCl Tolerance Agar | 14 days | | Tolerates 10% but not 13% NaCl | |
| Adenine Agar | 7 days | Good | Hydrolysis | |
| Guanine Agar | 7 days | Good | No Hydrolysis | |
| Hypoxanthine Agar | 7 days | Good | Hydrolysis | |
| Tyrosine Agar | 7 days | Good | Hydrolysis; melanoid pigment production | |
| Xanthine Agar | 7 days | Good | No hydrolysis | |

TABLE V

Carbon source utilization pattern of Streptomyces glaucogriseus NRRL 12514

Incubation: 14 days  Temperature: 28° C.

| Carbon Source | Utilization* |
|---|---|
| Adonitol | 3 |
| l-Arabinose | 2 |
| Dulcitol | 1 |
| Fructose | 2 |
| d-Galactose | 3 |
| d-Glucose | 3 |
| Glycerol | 0 |
| i-Inositol | 3 |
| Lactose | 2 |
| Maltose | 3 |
| d-Mannitol | 2 |
| d-Mannose | 2 |
| d-Melezitose | 0 |
| d-Melibiose | 3 |
| d-Raffinose | 2 |
| l-Rhamnose | 3 |
| d-Ribose | 2 |
| Salicin | 3 |

TABLE V-continued

Carbon source utilization pattern of
*Streptomyces glaucogriseus* NRRL 12514

| Incubation: 14 days | Temperature: 28° C. |
|---|---|
| Carbon Source | Utilization* |
| Sucrose | 2 |
| d-Trehalose | 2 |
| d-Xylose | 2 |
| Negative Control | 0 |

*3 = Good utilization
2 = Fair utilization
1 = Poor utilization
0 = No utilization It is to be understood that for the production of the antibacterial agent nosiheptide, the present invention is not limited to this particular organism or to organisms fully answering the above growth and microscopic characteristics, which are given for illustrative purposes only. In fact, it is desired and intended to include in the term "*Steptomyces glaucogriseus*, sp. nov., NRRL 12514" the natural (spontaneous) mutants of this organism as well as induced mutants produced from this organism by various mutagenic means known to those skilled in the art, such as exposure to X-ray radiation, ultraviolet irradiation, nitrogen mustard, actinophages, nitrosamines and the like. It is also desired and intended to include inter- and intra-specific genetic recombinants produced by genetic techniques known to those skilled in the art, such as, for example, conjugation, transduction, and genetic engineering techniques.

FERMENTATION PROCESS

Cultivation of *Streptomyces glaucogriseus* NRRL 12514 may be carried out in a wide variety of liquid media. Media which are useful for the production of this antibacterial agent include an assimilable source of carbon such as starch, sugar, molasses, glycerol, etc.; an assimilable source of nitrogen such as protein, protein hydrolysate, polypeptides, amino acids, corn steep liquor, etc.; and inorganic anion and cation salts, such as potassium, sodium, ammonium, calcium, sulfate, carbonate, phosphate, chloride, etc. Trace elements such boron, molybdenum, copper, etc. are supplied as impurities of other constituents of the media. Aeration in tanks, bottles and flasks is provided by forcing sterile air through or onto the surface of the fermenting medium. Further agitation in tanks is provided by a mechanical impeller. An anti-foaming agent such as lard oil or silicone defoamer may be added as needed.

INOCULUM PREPARATION

Shaker flask inoculum of *Streptomyces glaucogriseus* NRRL 12514 is prepared by inoculating 100 ml portions of sterile liquid medium in 500 ml flasks with scrapings or washings of spores from an agar slant of the culture. The following is an example of a suitable seed medium:

| Corn starch | 1.2% |
|---|---|
| Dextrose | 0.6% |
| Beef extract | 0.3% |
| Yeast extract | 0.5% |
| Bacto ®-tryptone[1] | 0.5% |
| Calcium carbonate | 0.2% |

[1]A peptone, registered trademark of Difco Laboratories, Detroit, Michigan

The above ingredients are added to an appropriate amount of water, the pH is adjusted to 7.5 with an alkali metal hydroxide and the mixture is sterilized prior to inoculation. These flasks are incubated at 24°–35° C., preferably 28° C., with agitation at 210 r.p.m. for 40–56 hours and are then used to inoculate 12 liters of the same sterile medium in a bottle, which after incubation with aeration by a sterile air flow of 2.0 liters per minute at 24°–35° C., preferably 28° C., for 40–56 hours is used to inoculate 300 liters of the same sterile medium in a seed tank. This inoculum is incubated at 24°–35° C., preferably 28° C., for 24 hours with aeration by a sterile air flow of 150 liters per minute and impeller agitation at 200 r.p.m. and then used to inoculate tank fermentors.

TANK FERMENTATION

The following is a suitable medium for the production of nosiheptide in fermentation tanks:

| Corn starch | 3.0% |
|---|---|
| Molasses | 2.0% |
| Soy peptone | 0.75% |
| Yeast extract | 0.25% |

The appropriate portions are mixed with sufficient water to make 3000 liters, sterilized, adjusted to pH 7.0–7.6, preferably pH 7.2, and inoculated with 3 to 10% of inoculum prepared as described above. Sterile aeration is supplied at 1650 liters of air per minute and the mixture is agitated by an impeller driven at 100 r.p.m. Defoamer is added when necessary. The temperature is maintained at 24°–35° C., preferably 28° C. The fermentation is continued for 40–140 hours, at which time the mash is harvested.

The invention will be described in greater detail in conjunction with the following non-limiting examples.

EXAMPLE 1

Inoculum Preparation

An inoculum medium is prepared according to the following formulation:

| Corn starch | 3,600 g |
|---|---|
| Dextrose | 1,800 g |
| Beef extract | 900 g |
| Yeast extract | 1,500 g |
| Bacto ®-tryptone | 1,500 g |
| Calcium carbonate | 600 g |
| Water qs ad | 300 liters |

This medium is adjusted to pH 7.5 with the addition of 75 ml of 6 N sodium hydroxide and then sterilized at 120° C. for 60 minutes.

Washed or scraped spores from an agar slant of *Streptomyces glaucogriseus* NRRL 12514 are used to inoculate 500 ml flasks containing 100 ml of the above sterile medium. The flasks are placed on a rotary shaker and agitated at 180 r.p.m. at 28° C. for 48 hours. The resulting flask inoculum is transferred to a 12-liter bottle containing the same sterile medium and incubated at 28° C. for 48 hours with sterile aeration. The resulting bottle inoculum is used to inoculate a tank containing 300 liters of the same sterile medium. The tank is then incubated at 28° C. for 24 hours with impeller agitation at 200 r.p.m. and aeration supplied by a sterile air flow of 150 liters per minute, producing a tank inoculum.

EXAMPLE 2

Fermentation

A fermentation medium is prepared according to the following formula:

| Corn starch | 90 Kg |
|---|---|
| Molasses | 60 Kg |
| Soy peptone | 22.5 Kg |
| Yeast extract | 7.5 Kg |
| Water to | 3,000 liters |

This fermentation medium is adjusted to pH 7.2 with 6 N sodium hydroxide, sterilized at 120° C. for 60 minutes and then inoculated with 300 liters of the tank inoculum prepared in Example 1. The fermentation is carried out at 28° C., using Hodag FD-82 ® [a silicone antifoam, registered trademark of Hodag Chemical Corp., Skokie, Ill.] as a defoaming agent. Sterile aeration is supplied at 1650 liters of sterile air per minute. The mash is agitated by impellers driven at 100 r.p.m. At the end of approximately 120 hours of fermentation time, the mash is harvested.

EXAMPLE 3

Preliminary Isolation of Nosiheptide

A fermentation is carried out as described in Example 2. The 2700 liters of harvest mash is divided into two equal volumes. To each is added an equal volume of methylene chloride. The methylene chloride is cycled from the bottom of each container down through the mash for a period of 2 hours. The phases are allowed to separate for 1½–2 hours and then the clear methylene chloride extract is withdrawn. This extract is concentrated in several stages to a syrup, giving 876 g of the crude product.

EXAMPLE 4

Isolation of Nosiheptide

The 876 g of crude product from Example 3 is triturated with three pints of ether for ½ hour. The ether is decanted through a filter and the filter is washed with ether. The residue on the funnel and the residue in the trituration flask are dissolved in methanol. The methanol solutions are combined and concentrated in vacuo, giving 152 g of a semi-solid.

A column with a diameter of 8.5 cm is packed to a height of 75 cm with silica gel. The 152 g of semi-solid is dissolved in 300 ml of methylene chloride: ethyl acetate (1:1) and allowed to seep into the column. The column is developed with 4 liters of ethyl acetate: methylene chloride (1:1) and then methylene chloride: ethyl acetate:methanol (6:6:1). Fractions of 90 ml each are collected, and checked for activity by bioautography against *Straphylococcus aureus* 209P. Fractions 142–207 are combined and lyophilized, giving 22 g of solid.

A column with a diameter of 8.5 cm is packed to a height of 82 cm with silica gel. The 22 g of solid is dissolved in 200 ml of chloroform:ethyl acetate (1:1) and allowed to seep into the column. The column is first eluted with 3 liters of chloroform:ethyl acetate (1:1), collecting fractions of 65 ml each. The eluting solvent is changed to ethyl acetate:ethanol (95:5) for the remaining 65 ml fractions. A total of 160 fractions are collected, checking for activity by bioautography. Fractions 78–102 are combined and concentrated in vacuo to a 50 ml suspension. This suspension is filtered and the solid is washed with ether and are dried, giving 864 mg of nosiheptide.

A 133 mg portion of the above amorphous solid is dissolved in 5 ml of glacial acetic acid and then filtered. A 0.5 ml portion of acetone is added to the filtrate and this solution is chilled at 4° C. overnight. The resulting suspension is filtered cold and the solid washed with ether and dried giving 93 mg of crystalline nosiheptide.

We claim:

1. A process for preparing the antibiotic nosiheptide, having the formula:

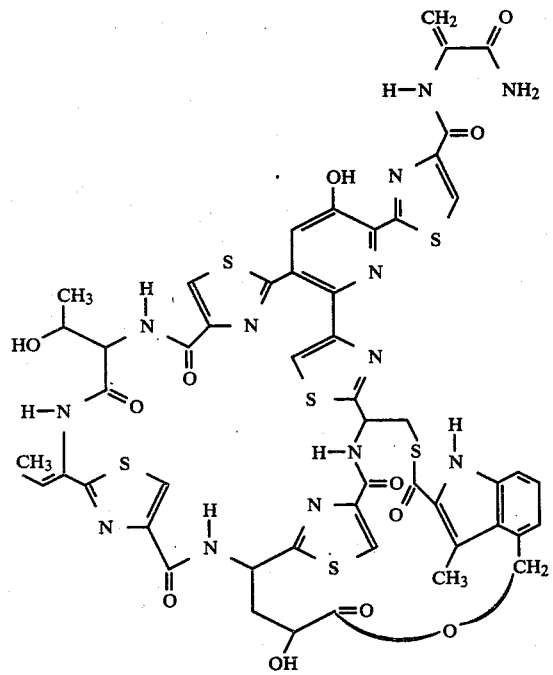

which comprises cultivating *Streptomyces glaucogriseus,* having the identifying characteristics of NRRL 12514, and the nosiheptide-producing mutants thereof, under aerobic conditions, in a sterile liquid medium containing assimilable sources of carbon, nitrogen and inorganic anion and cation salts, until substantial antibiotic activity is imparted to said medium by the production of nosiheptide and then recovering the antibiotic therefrom.

2. A process for preparing the antibiotic nosiheptide which comprises aerobically fermenting a liquid medium containing assimilable sources of carbon, nitrogen and inorganic anion and cation salts, which medium has been inoculated with a viable culture of *Streptomyces glaucogriseus,* having the identifying characteristics of NRRL 12514, and the nosiheptide-producing mutants thereof, maintaining said fermentation culture with sterile aeration and agitation, at a pH of 7.0–7.6, for a period of 40–140 hours at 24°–35° C., harvesting the mash, extracting the crude product in methylene chloride and purifying by conventional chromatography.

3. The process according to claim 2, wherein the pH of the liquid medium is 7.2.

4. The process according to claim 2, wherein the temperature of the fermentation is carried out at 28° C.

5. A biologically pure culture of the microorganism *Streptomyces glaucogriseus,* sp. nov., having the identifying characteristics of NRRL 12514, said culture being capable of producing the antibiotic nosiheptide in recoverable quantity upon fermentation in an aqueous nutrient medium containing assimilable sources of carbon, nitrogen and inorganic anion and cation salts.

6. The biologically pure culture of the microorganism *Streptomyces glaucogriseus*, sp. nov., according to claim 5, wherein the microorganism has spontaneously mutated such that the microorganism is genetically altered but still retains the ability to synthesize the antibiotic nosiheptide.

7. The biologically pure culture of the microorganism *Streptomyces glaucogriseus*, sp. nov., according to claim 5, wherein the microorganism has been subjected to mutagenic means such that the microorganism is genetically altered but still retains the ability to synthesize the antibiotic nosiheptide.

* * * * *